US006698028B2

(12) United States Patent
Daw

(10) Patent No.: US 6,698,028 B2
(45) Date of Patent: Mar. 2, 2004

(54) HEADPHONE EARMUFFS

(76) Inventor: Jeffrey Lewis Daw, 19066 Old Detroit Rd. Apt. 2E, Rocky River, OH (US) 44116

(*) Notice: Subject to any disclaimer, the term of this patent is extended or adjusted under 35 U.S.C. 154(b) by 0 days.

(21) Appl. No.: 10/080,725

(22) Filed: Feb. 22, 2002

(65) Prior Publication Data

US 2003/0159197 A1 Aug. 28, 2003

(51) Int. Cl.[7] .......................... A61F 11/06; H04R 5/033
(52) U.S. Cl. ........................................... 2/209; 381/371
(58) Field of Search ..................... 2/209, 423; 381/371, 381/374, 376

(56) References Cited

U.S. PATENT DOCUMENTS 1,396,771 A * 11/1921 Minton ...................... 2/209 X
2,403,418 A 7/1946 Volkmann
2,447,470 A 8/1948 Valentine
2,468,267 A * 4/1949 Mondl ....................... 2/209 X
2,468,721 A 4/1949 Volkmann
2,812,517 A 11/1957 Bogart
4,065,645 A 12/1977 Warner
4,243,851 A 1/1981 Forney
4,546,215 A 10/1985 Ferraro
4,654,898 A 4/1987 Ishikawa
4,669,129 A * 6/1987 Chance .......................... 2/209
4,670,911 A * 6/1987 Dunford ........................ 2/209
5,241,971 A 9/1993 Lundin
5,257,420 A * 11/1993 Byrne, Jr. ...................... 2/209
5,778,455 A 7/1998 Joseph
5,898,945 A 5/1999 Weiser

FOREIGN PATENT DOCUMENTS

FR 2536204 * 6/1984 .................... 2/209

* cited by examiner

*Primary Examiner*—Peter Nerbun

(57) ABSTRACT

The present invention relates in general to ear muffs and in particular to an earmuff that are to be used in conjunction with headphones for portable radios, cassette players and the like. The outer surface of the earmuff is a solid shape resembling a standard earmuff while the inner side that faces the ear breaks apart into 2 C-shape donut halves to accommodate the placement of the headphone speaker. This design allows the earmuff to be positioned around the headphone speaker by means of the 2 C-shape donut halves and reconnect together around the headphone speaker in order to stabilize against the headphone and allow space for the headphone band and speaker wire between the connected respective halves of the donut. The earmuff makes use of the unique donut design to accommodate various styles of portable headphones while providing maximum insulation to the ear. The earmuffs are detachable and can be exchanged. The earmuff in this invention can be made of various materials customary to cold weather clothing accessories, such as wool, cotton and the like. The earmuff is designed to encompass and protect the headphone speaker from weather elements as well as being made of materials high in insulating capacity and being of a size to envelop the ear of the wearer as well as the surrounding part of the head as is similar to the coverage and insulation provided by typical earmuffs on the market.

13 Claims, 5 Drawing Sheets

Inside Open with Headphones

Top View Closed with headphone speaker

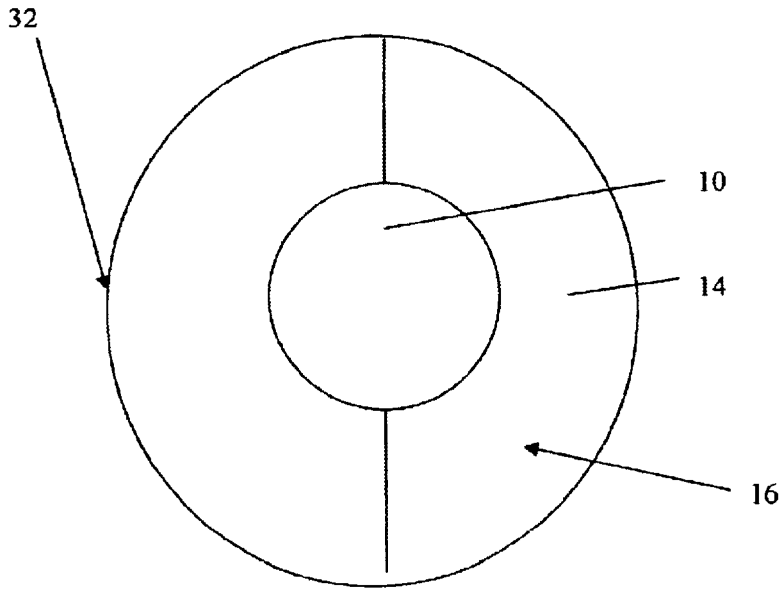
Fig. 1 Inside Closed
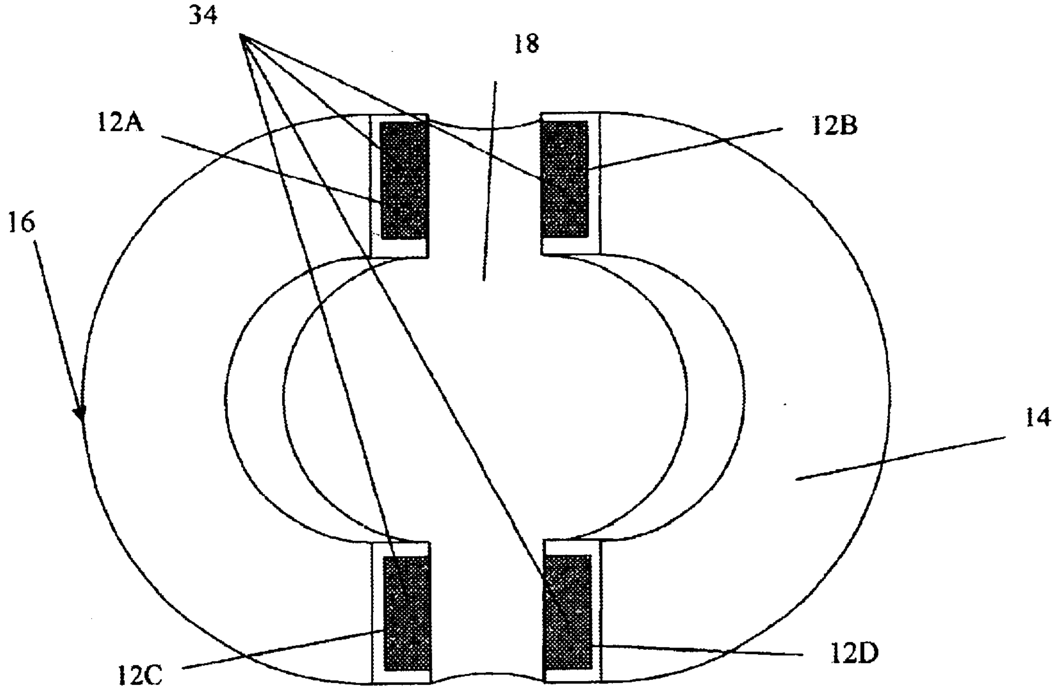
Fig. 2 Inside Open

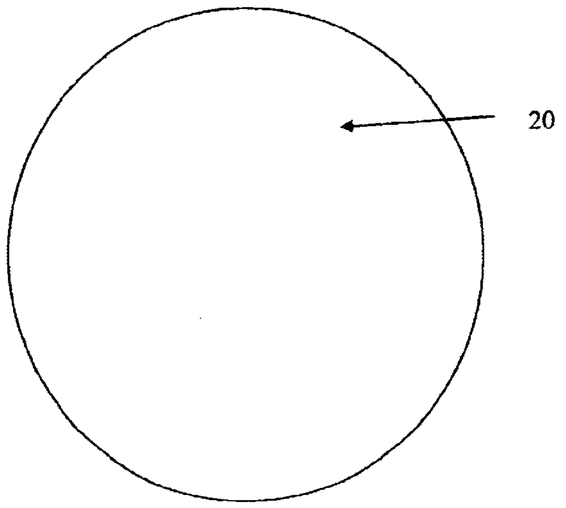
Fig 3. Outside View
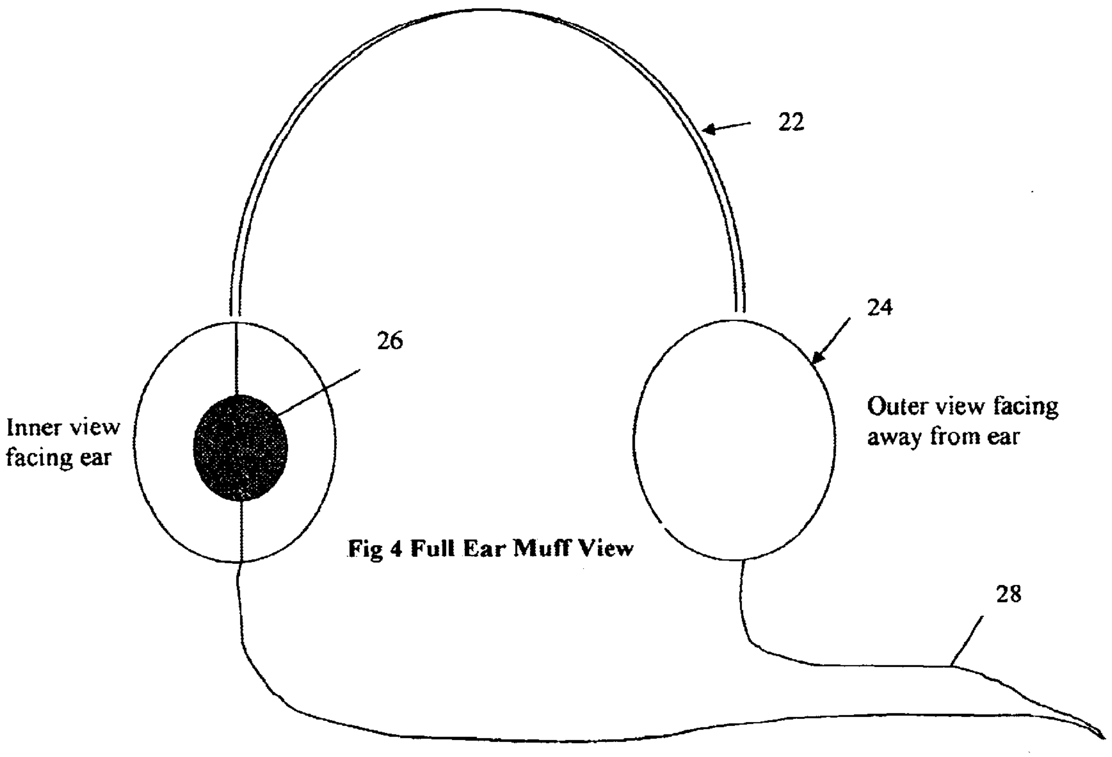
Fig 4 Full Ear Muff View

Fig. 5 Inside Closed with headphone
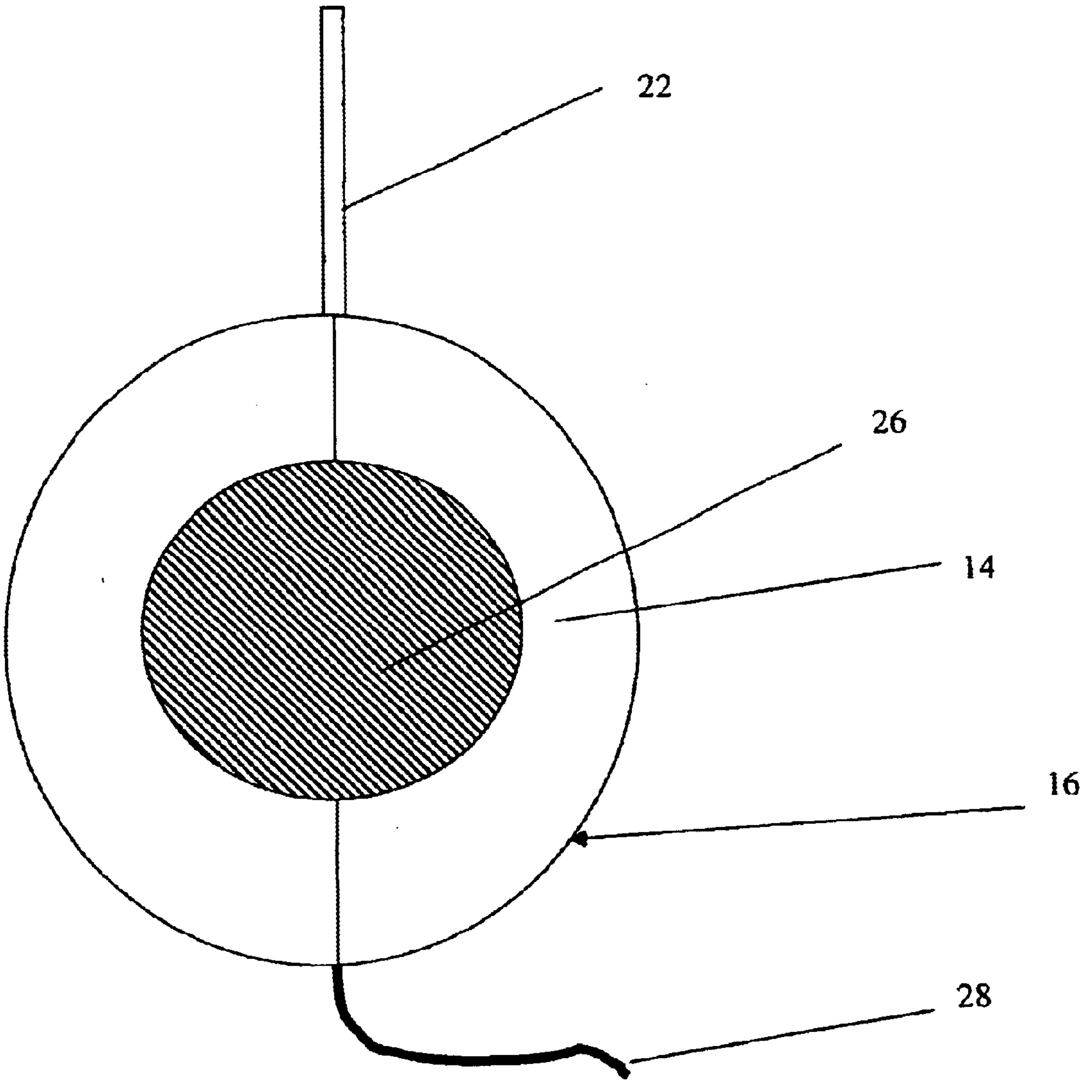

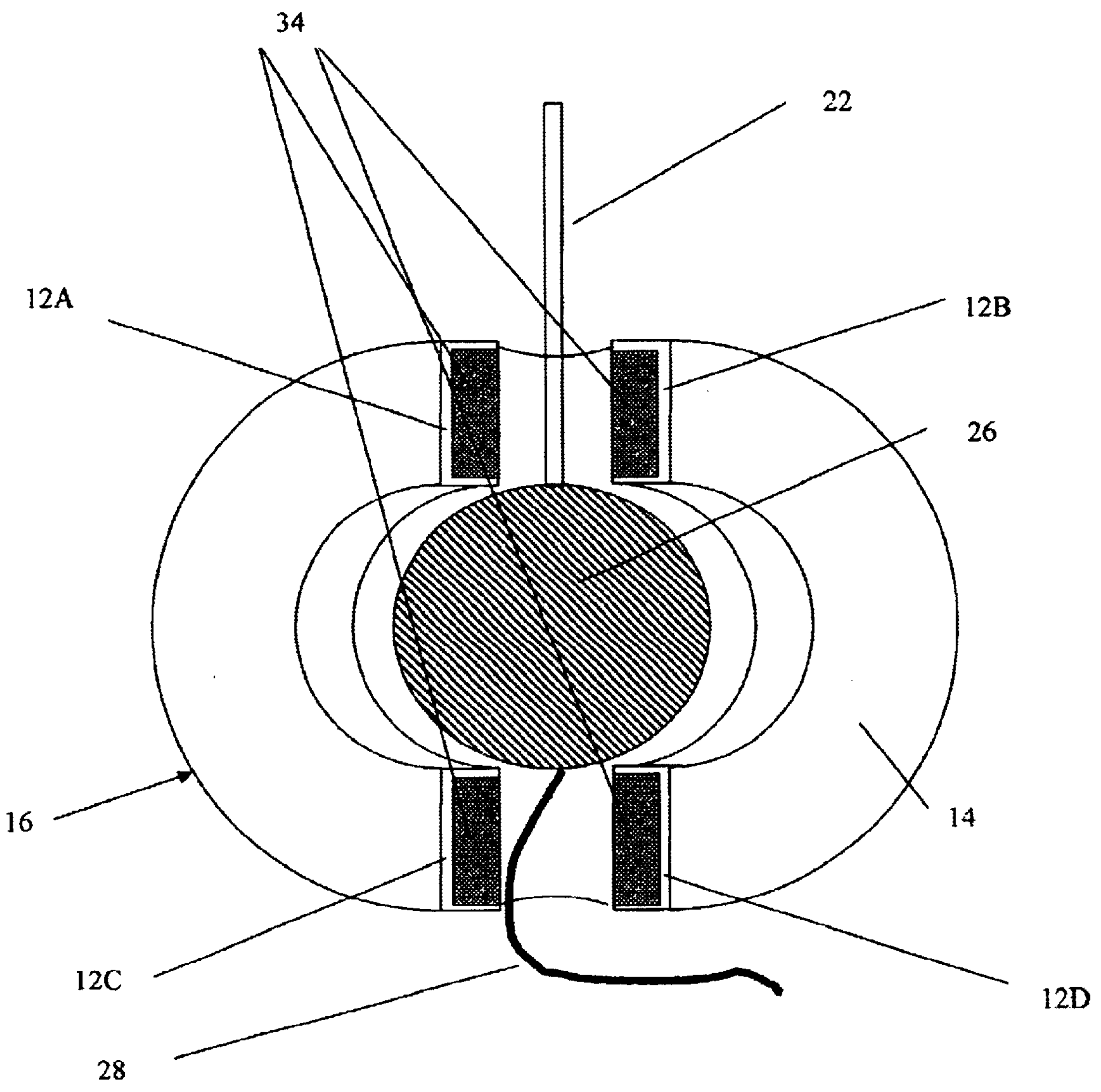
Fig. 6 Inside Open with Headphones

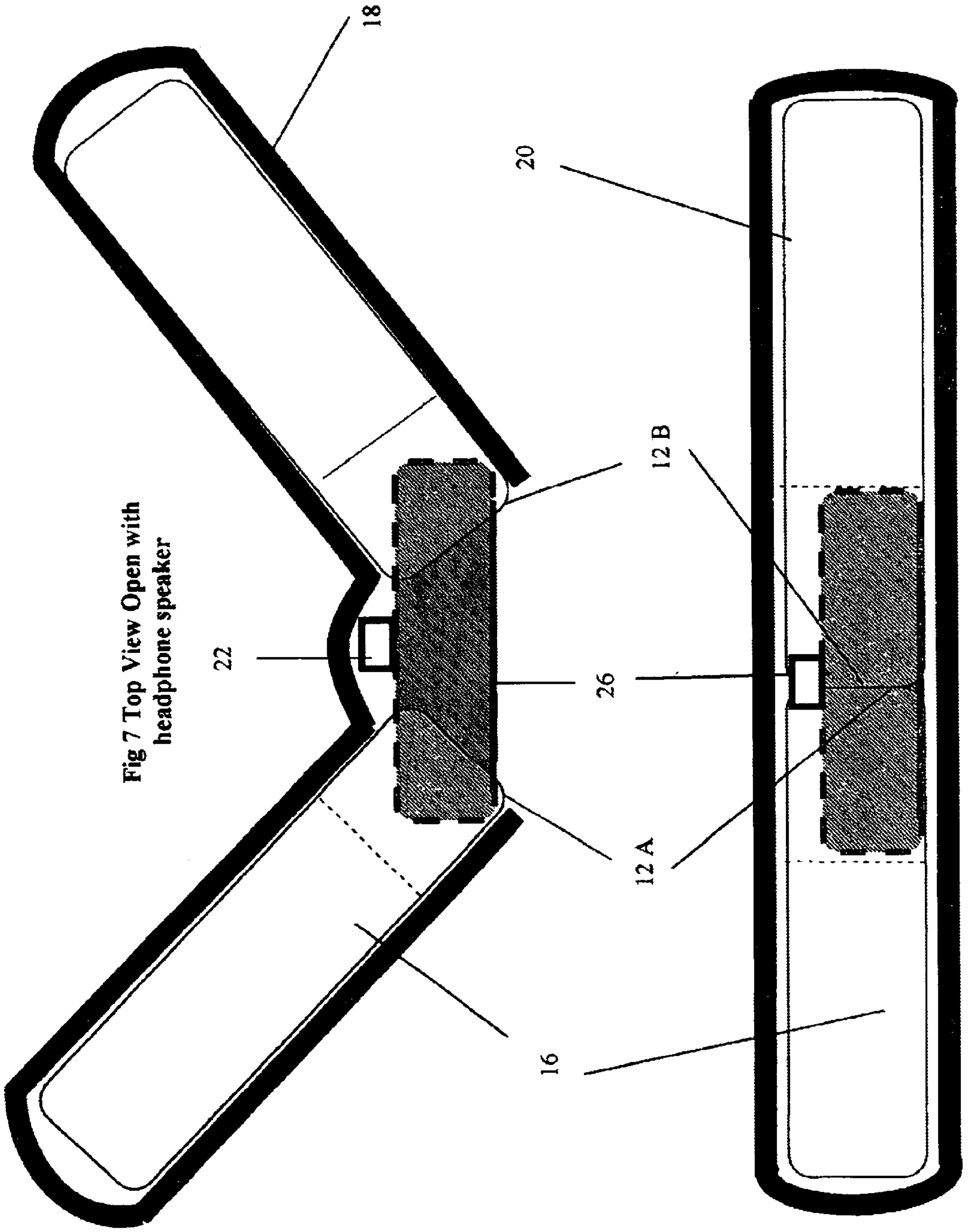
Fig 7 Top View Open with headphone speaker
Fig. 8 Top View Closed with headphone speaker

HEADPHONE EARMUFFS

CROSS-REFERENCE TO RELATED APPLICATIONS

Not applicable

BACKGROUND

1. Field of Invention

This invention relates in general to ear muffs, specifically to ear muffs that are to be used in conjunction with headphones for portable radios, cassette players and other media players of the like.

2. Description of Prior Art

The Earmuff originally was designed to protect the ears from cold weather. The Earmuffs consisted of two insulated cushions or muffs usually round or oval typically attached together with a flexible curved center section or band. The band extends over the head of the wearer and has at each end, the padded earmuff piece that is permanently affixed to be in register with the ear of the wearer.

For purposes of definition, the standard earmuff commonly available on the market today, will be defined to include the above description as well as the following features. The typical earmuff consists of two pads or muffs commonly filled with insulating padding and covered with an insulating material such as cloth, fur—synthetic or otherwise. The typical earmuff design is oversized in relationship to the ear in order to over both the ear and part of the head around the ear to ensure a comfortable and well-insulated fit.

In addition, devices also known as earmuffs have been used to provide acoustic protection to the ear of a wearer against excessive noise such as the sound of a firearm which is discharged or the sound of a jet engine. Devices known as headsets, earphones or headphones have been used to provide a means for positioning a speaker adjacent to the ear of the user while excluding background noise in order to facilitate the reception of sound. The headphone devices have typically been made with a flexible curved center section or band, which extends over the head positioning a speaker adjacent to the ear of the user while excluding background noise in order to facilitate the reception of sound.

Portable radios and cassette players with small portable speakers are very popular. The speakers that accompany these portable players are usually small and lightweight and are designed to fit on the ear comfortably with their circumference well within the area of the ear. Due to their size and construction the speakers do not lend themselves to protecting the ear against cold weather. Larger headphones do exist that completely cover the ear, but do not have the design elements necessary for proper insulation in cold weather and they are considerably larger, heavier and more expensive to be practically adapted for outdoor use.

The construction of the headphone is very similar to the earmuff. It consists of two speakers that are connected by a curved center section, typically referred to as a band, which extends over the head of the wearer much like the ear muff, and is designed to hold the speakers adjacent to each ear the same way ear muffs are held over the ears by a band.

The two devices cannot be used together for the following reasons. Earmuffs do not have the space required to accommodate headphone speakers so that the headphone speakers could be placed adjacent to the ear while the earmuffs are also occupying the same adjacent space next to the ear. Earmuffs and headphones make use of a band to position their respective end pieces, either muff or speaker adjacent to the wearers ear. Using both in unison becomes difficult due to the multiplicity of bands and earpieces. The fitting of one set of ear pieces adjacent to the ear naturally prevents the placement of the other to the same.

Several types of headphone earmuffs have been proposed in the past to accomplish the task of insulating the ear while wearing headphones, but with inherent disadvantages.

Due to the popularity of headphones and portable listening devices such as radios, cassette, compact disc, and media devices of the like, many styles of headphones have become available and are currently in use. Each style of headphone boasts a unique design as well as materials. The variances between models range in the areas of speaker size and shape, as well as the different band consistencies and their connection methods to the speakers they support. Prior art does not allow for the use of the headphone earmuff with the wide variety of headphones already available on the market.

The connection method which secures the earmuff to the headphone speaker unit in U.S. Pat. No. 4,546,215 depends on the band of the headphone unit to be of a specific dimension as well as in one predefined relationship to the headphone speaker which must be of a specific size and circumference in order to connect the earmuff to the headphone speaker. Any variation in speaker size, bandwidth or girth or angle of connection between the band and earphone speaker will render the design in U.S. Pat. No. 4,546,215 unusable. Additionally, the design in U.S. Pat. No. 4,546,215 limits the size of the earmuff because it is constructed with a spring loop that defines the circumference of the earmuff. The earmuff has inter-linking ends that comprise the connecting mechanism of the muff, which must stay in close relationship with the connecting point of the band and the speaker in order to prove effective. If the ring is made larger to accommodate an oversized ear muff consistent with the standard earmuff designs in the market today, the ring must still connect with the headphone at the same juncture where band and speaker meet making the enlarged earmuff hang well below the ear and not equally around it as an efficient use of an earmuff dictates.

Further by having a limited size and shape dictated by the patent's design, the aesthetic features commonly associated with the popularized earmuffs found in the market wherein a soft plush round or oval insulated pad being oversized to the ear touching the surrounding area of the head is featured, is compromised in order to achieve this patent's perceived function. In conclusion, the design above in U.S. Pat. No. 4,546,215 limits its uses with the various styles of headphones on the market having only the capability to work in conjunction with a few that meet its limited physical dimension criteria.

In prior art U.S. Pat. No. 4,654,898 the earmuff designed to be used in conjunction with headphones features two rounded flaps the intended to be secured flatly together sandwiching the earphone in between them. The flaps are fastened together by matching hook and loop fasteners or the like. It is thus required to match the opposing flaps in exact symmetry to each other while sandwiching the speaker at the same time in order to properly place the headphone speaker within the earmuff. It is apparent by this designs functionality that it requires complex manipulation of the matching pieces to properly align and therefore use this item. In addition, once the flaps are properly in place, small adjustments necessary to keep the earmuff in proper alignment with the headphone speakers proves difficult due to the fact that the two flaps completely encase the headphone speaker and there for allow for little movement with out the need to completely separate and reattach the flaps together in new alignment.

The design in U.S. Pat. No. 4,654,898 lacks the internal structure that would otherwise prevent the earphone from twisting inside the pocket created by the two-sandwiched flaps. Proper positioning of the earphone inside the sandwich pocket is possible, but due to the lack of structure and support proves difficult to maintain. The standard earmuff typically features oversized earmuff pads which surround the ear and lie in contact with the area of the head around the ear in order to completely cover and insulate the wearers ear and ear region of the head. U.S. Pat. No. 4,654,898's use of flaps as described above make use of a thin cupped shape covered by material that engages the ear in order to provide insulation. The cup is not shown to contact the head and thus does not envelope the ear nor is there mention that the design features insulation of any kind outside of the aforementioned cloth material. This lack of insulation and respective area coverage around the ear proves inadequate as a proper insulating device in extreme cold weather.

Both patents mentioned above go about solving the problem of encasing the headphones within the earmuff by means of forming a pocket with which the headphone speaker is to occupy. It is by the creation of this pocket, either by the matching of cloth flaps in U.S. Pat. No. 4,654,898 or a cloth pocket framed by a spring loop, in U.S. Pat. No. 4,546,215, that both designs fail to provide adequate insulation necessary to protect the ear and surround area of the head. By having a pocket as the center of the earmuff to accommodate the speaker the space is no longer available for insulation. And due to size restrictions inherent in each design, there is little space and or surface area available to adequately be used for insulating the ear. Both designs depend on cloth such as wool with insulating properties to do the job of keeping the ears of the wearer warm. In extreme cold conditions the designs will not match the insulating efficiency of a fully padded earmuff.

In other items of prior art, earmuffs and headphones are featured together as one invention. The earmuffs are designed to attach exclusively to its headphone counterpart. The earmuff can not be used with other headsets on the market due to this design. This design does not fall within the range of inventions of earmuffs designed to fit headphones, but an invention incorporating both headphone and earmuff together. Therefore, this type of prior art does not provide an earmuff designed to be used with the variety of headphones on the market as my invention does.

In conclusion, prior art earmuffs built to accommodate headphone speakers have not solved the problem of incorporating the headphone speaker inside the earmuff without sacrificing insulation and or allowing the muff to be any size or shape. In addition, the designs of prior art have failed to make an ear muff capable of being used with the many styles and shapes of portable headphones on the market. In addition, prior art incorporates designs that either inconvenience the user with their complexity having such things as flaps to align and maintain as in U.S. Pat. No. 4,654,898 or spring loops to snap over one style of headphone as in U.S. Pat. No. 4,546,215. These designs are inconvenient to users that choose different headphone styles.

Further, the prior art discussed cannot be made into shapes such as triangles or squares or enlarged circles due to their design limitations. Typical earmuffs cover more than just the ear in order to be effective. The typical earmuff design is intended to be oversized in relationship to the ear in order to cover both the ear and part of the head around the ear to ensure a comfortable and well-insulated fit. The typical earmuff is commonly filled with insulation and covered with an insulating material. The prior art discussed above is limited both in design as well as use of materials for accomplishing the same usefulness as the standard earmuff described here. By showing how prior art compares with the functionality of a typical earmuff and noting disadvantages concerning their respective designs, it will become obvious how my headphone earmuff design encompasses and solves many of the issues presented.

SUMMARY

The headphone earmuff is designed to allow for listening to music through portable headphones while having the ears protected from cold weather by an earmuff that surrounds the headphones and is in register with the ears and surrounding region of the head.

The headphone earmuff is band less, unlike conventional earmuffs, but otherwise is constructed of like materials possessing insulating qualities and materials that accomplish the same.

The headphone earmuff uses the stereo headphones connecting band to position and hold in place said earmuffs adjacent to the wearers ears while using the headphone speakers as a positioning anchor to maintain proper alignment.

The headphone earmuff in my invention is designed specifically to be used with a wide variety of portable headphone designs already available and widely used on the market.

The headphone earmuff does not require a specially designed attachment system between the earmuff and headphone to combine the two.

The headphone earmuff in my patent can be oversized to accommodate both the ear and the surrounding head area similar to standard earmuff designs.

The design of my earmuff for portable headphones allows for an abundance of insulation and insulating materials.

My design features a simple closing mechanism of facing hook and loop fasteners to secure the earmuff around virtually any style of headphone speaker and its band without sacrificing the ability to make adjustments while wearing the earmuff on the headphones.

My design accomplished the purpose of an attachable earmuff for the use with portable headphones without complex connecting mechanisms or structural design elements that require precise manipulation.

My design can be used with virtually any design of portable headphone on the market The earmuffs in my patent can be closely patterned after the standard ear muff in order to accomplish design, utility, and aesthetic advantages in regards to like materials, like insulating properties and similar look feel and product identity that users of the standard earmuff are already used to.

The headphone earmuff may also be patterned in a variety of shapes and materials to suit different uses for all types of environments including but not limited to rain, snow, cold, and the like as well as constructed out of alternative materials to suit users preferences as well as purposes which are defined by environment and or have not been identified yet.

OBJECTS AND ADVANTAGES

Accordingly, several objects and advantages of the headphone earmuff are:

(a) Allowing for the listening of music through portable headphones in cold weather while protecting the ears and bead area around the ears from the cold.

(b) Protecting the earphones themselves from weather elements such as cold, and moisture.
(c) Uses the portable headphones as a supporting structure using the connecting band of the headphone to position and stabilize the headphone earmuff over the wearer's ears while using the speakers to affix to.
(d) Allowing for adjustments while in use for optimum comfort and fit.
(e) Simple to operate and machine washable.
(f) Can be created in any size shape or pattern for aesthetic, practical, and utilitarian considerations.
(g) Earmuffs are not required to have a connecting strap to hold them in place over the ears.
(h) The headphone earmuffs are more compact than normal earmuffs due to the lack of connecting band.
(i) It is possible to mix and match with other sets of headphone earmuffs due to the individual muffs being separate and being individually attachable to each speaker headphone.
(j) Can be used with a wide variety of portable headphone designs available on the market.
(k) Aesthetically similar to earmuffs already on the market.
(l) Does not require special connections or intricate manipulations for use
(m) The headphone earmuffs can be made from any cloth material and the like.
(n) Provides more than adequate insulation for extreme weather conditions.
(o) The headphone earmuff has a semi-rigid internal structure that serves as a resilient shape for the earmuff that protects the ears as well as the headphones of the user from environmental abuses.
(p) The structure that comprises the form of the earmuff provides for a secure fit and placement for the speaker inside the earmuff in order to dramatically reduce random repositioning of said speaker during use.

Further objects and advantages of the headphone earmuff will become apparent from a consideration of drawings and ensuing description.

DESCRIPTION OF DRAWINGS

FIG. 1 is a perspective view of the inside (side that faces the ear) of the headphone earmuff. It is a basic donut shape constructed of foam or like material, which is divided in half and reconnected. The donut divides into the C-shapes in order to provide space for the headphone speakers and reconnects around each speaker.

FIG. 2. The headphone earmuff is in an opened position showing how each side (donut halves) open to receive the headphone speaker. The headphone speaker space accommodates most models of earphone speakers. The facing sides of the split donut fasten together around the headphone speaker and headband in the original donut shape. This allows the headphone muff to hug the speakers while staying in position and use the speaker's headband to stay in position around the head. In addition, the planar connecting donuts sides separate and reconnect respectively to allow for the positioning of the speaker wire, allowing it to pass through the earmuff. The donut halves are connected with material on their back side allowing the donut halves to swing open to allow speaker to be positioned on the inside.

FIG. 3. Shows the outside of the headphone earmuff while closed. It looks like a regular earmuff except for the lack of a connecting strap. The headphone earmuff is covered with insulating material, fuzzy or otherwise. Note there is not evidence of the split donut as seen on the in FIG. 2. As indicated in the description of FIG. 2 above, the donut splits and hinges open on one the inside to allow for headphone speaker placement, however on the outside (FIG. 3) both donut halves are covered with material resembling the standard earmuff, thus the donut hinges on the outside material opening on the inside (FIG. 2) while retaining the earmuff form with the material on the outside.

FIG. 4. Shows the headphone earmuff connected to portable stereo headphones. As indicated the headphone ear muffs enclose around the speaker reconnecting each side of the donut with the hook and loop fasteners that encircle the band of the headphones on top and the wire back to the media player on the bottom. The earmuff fully surrounds the headphone speaker insulating it and the ear from the cold weather keeping the inner side open to allow the speaker to rest against the ear for maximum listening pleasure. Together the headphone earmuff serves as an earmuff and headphone accessory useful in cold weather. FIG. 4 shows on the left side the inside view of the earmuff around the headphone speaker. The right side of FIG. 4 shows the outer view of the earmuff.

FIG. 5. shows the inside view of the headphone earmuff with the headphone placed inside. The donut halves are closed around the speaker allowing between the facing halves of the split donut, the headphone speaker on top and the wire below.

FIG. 6. Shows the inside view of the headphone earmuff in the open position revealing how the headphone speaker, band and wire are placed in the earmuff before it is closed.

FIG. 7. Shows the open view of the earmuff as indicated in FIG. 2 from the top of the split donut. It shows the donut hinged open to allow the placement of the headphone and indicates how the material on the outside of the ear muffs acts as a hinge allowing the donut to open.

FIG. 8. Shows the closed view of the earmuff as indicated in FIG. 1, from the tops of the split donut in its closed position showing how the headphone speaker is positioned inside the earmuff. The dotted lines on the earmuff show that there is a center section hollowed out for the placement of the headphones within the earmuff. The dotted lines around the headphone speaker indicate that they are enclosed within the two halves of the donut in the center.

List of Reference Numerals

| | |
|---|---|
| 10 | Headphone Speakers Space |
| 12 | Planar sides that connect. |
| 12a | Planar sides top left |
| 12b | Planar side top right |
| 12c | Planar side bottom left |
| 12d | planar side bottom right |
| 14 | Inside Planar Surface |
| 16 | C-shape half donut. |
| 18 | Backing |
| 20 | Outer Surface |
| 22 | Connecting Head Band |
| 24 | Headphone Earmuff |
| 26 | Headphone Speaker |
| 28 | Speaker Wire |
| 30 | Foam Donut |

DESCRIPTION OF INVENTION

FIG. 1 shows a perspective view of the headphone earmuff. The inner structure is constructed out of foam material or the like of a thickness that is rigid enough to hold the shape of a round disk cut in half and bored out in the center so that the structure is that of a donut cut in half. The two halves of the foam donut are then fastened together with hook and loop type fastener. A speaker space 10 in the middle is created when the two-donut halves 16 are fastened together. This speaker space 10 is occupied with a headphone speaker 26 where a band 22 follows between planar sides 12*a* and 12*b* at the top of the connecting donut. Planar sides 12*c* and 12*d* at the bottom of the split donut reconnect around the headphone speaker 26 and speaker wire 28 allowing it to exit the earmuff.

An outer covering of the foam donut, comprised of the connecting C shape halves 16, is covered with fabric on its outer surface 20 said fabric enclosing each donut half 16, whether in open position or closed. Backing 18, FIG. 2 connects both donut halves 16 together as they open and close. This backing serves as the outer surface of the headphone earmuff as well as the connecting fabric keeping both donut halves from separating completely. In this fashion the backing 18, FIG. 2 allows the donut halves to swing open in FIG. 2 allowing the placement of the speaker 26, FIG. 4 and enclose the donut halves around the respective speakers by connecting together again.

The back covering 18 covers both donut halves together resembling that of a disk and wraps around each donut half, 16 and following the contour of the inside of each donut, thus creating a space 10 that is not covered by material that is used for speaker placement, the headphone speaker space 10. On the outside of the headphone earmuff, FIG. 3 the two donut halves 16 are covered together comprising the outer surface 20 and resembling said disk.

Each foam donut half 16 connects together with hook and loop type fasteners that are adhered to the planar surfaces 12*a*–12*b*, and 12*c*–12*d* mating each planar surface respectively allowing each donut to fasten together.

When the donut halves 16 are closed in FIG. 3 the outside is one form (an oval shape in the figure). The inside of this connected oval FIG. 1 connected together by hook and loop fasteners on planar sides 12*a* through 12*d* surrounds the headphone speaker 26 that has been placed in the speaker space 10. This closed form that is closed around each speaker is then used in conjunction with the speakers as they are worn over each ear allowing speakers to be against the ears as well as having the surrounding headphone earmuffs insulating the ears.

OPERATION OF INVENTION

The headphone earmuff functions as an earmuff that surrounds a headphone speaker serving to insulate the wearers' ears while allowing the use of headphones. Each muff is constructed as a fabric covered foam donut that is split in half into C shaped half donuts 16 and reattached together at the meeting planar edges 12*a* through 12*d* with a hook and loop type fastener 34. The donut is covered by material completely on the outside of the form to resemble an oval, while the inside covers cover each donut half following the contours of each half to allow for a space resembling a circular hole only on the inside of the donut form providing space for speaker placement. The donut can then be "broken" apart hinging on the backing 18 to open and receive a headphone speaker into its headphone speakers space 10. On the inside of the donut as shown in FIG. 2, the planar sides 12*a*, 12*b*, 12*c*, 12*d*, connect the C-shape half donuts 16 around the speaker space 10 and allow for the headphone band to pass through the pathway between planar edges 12*a* and 12*b* and allowing the speaker wire to pass out at the bottom between planar edges 12*c* and 12*d* as they connect in order to allow the muff to wrap around the headphone speaker and serve as an earmuff.

Each donut half is attached by hook and loop fasteners connected at the edges when the muff is closed. When pulled apart the earmuff hinges on the backing 18 or outer surface 20 like a hinge to allow the headphone to be placed through the inside of the earmuff and the halves around it.

CONCLUSION, RAMIFICATION SCOPE OF INVENTION

Thus the reader will see that the headphone earmuff is an invention that provides a well insulated, lightweight, convenient easy to use headphone earmuff that can be used by people of almost any age. While the above description contains much specificity, these should not be construed as limitations on the scope of the invention but rather as an exemplification of one preferred embodiment thereof Many other variations are possible. For example, different sizes and shapes of stereo headphone earmuffs may be constructed to accommodate different styles and shapes of headphones while maintaining the same utility as this design indicates. Although, the unique manner in which the headphone earmuff in this invention accommodates almost any style of portable headphones, size and shape considerations for style purposes as well as marketing are to be considered within the scope of this invention.

The headphone earmuff may also be constructed of various materials colors or shapes and used for purposes other than cold weather. The muff may be constructed to accommodate all conceived conditions and applications for the uses with headphones. The headphone earmuff may be made to suit all applications and uses mentioned, but not limited to the descriptions and purposes Accordingly, the scope of this invention should be determined not by the embodiments illustrated but by the appended claims and their legal equivalents.

What is claimed is:

1. An earmuff securable in a releaseable manner to a portable headphone speaker headset unit that is adapted to be worn on a person's head wherein said headset has an earphone and a headband operative to bias the earphone against the ear, comprising:

a) a donut shaped core element having an outer surface, inside planar surface that is divided into two C shape half donut sections whereby said C shape half donut sections separate and reconnect along their division, a central hole formed by the connection of said C shape half donut sections at their division; and b) said central hole defined as the headphone speaker space that is formed between the said C shape half donut sections when connected, said hole being sized to receive said headphone speaker whereby said C shape half donut sections separate along their division and reconnect around said headphone speakers in a manner as to bias the headphone speaker within said headphone speaker space central to the donut shaped core element whereby said headphone speaker is directly adjacent to ear surrounded by the inside planar surfaces also adjacent to the ear; and c) said donut shaped core element is of substantial thickness from outer surface to inside planar surface to accommodate headphone speaker thickness; and d) planar sides defined as the area of said C shape half donut sections that face each other when said C shape half donut sections connect to each other; and e) cooperative connection means comprised of hook and loop fasteners located on said planar sides for releaseably securing said C shaped half donut sections together at their division whereby the headphone speaker is retained located within the said the headphone speaker space and is biased to a location adjacent to the ear with the C shape half donut sections surrounding the headphone speaker; and f) a backing comprised of fabric that is closely fit to and is coextensive to said donut shaped core element on its outer surface; and g) said backing extends around the outside perimeter of said C shape half donut sections and across inside planar surface of each C shaped half donut section closely fitted and coextensive to their respective C shapes allowing the division between them and closely fitted to the sides of said headphone speaker space; and h) whereby said C shape half donut sections hinge apart and together by means of said backing extending across the outer surface of said donut shaped core element to receive said headphone speaker between the said C shape half donut sections; and i) a headphone speaker space which is defined by the hole that is formed within the inner curvature formed by said C shape half donut sections whereby a hole centrally within the donut shaped core element is formed that receives the headphone speaker; and j) the donut shaped core element is defined by the connection of the C Shaped half donut sections at their planar sides and secured by cooperative connection means comprised of hook and loop fasteners located on said planar sides.

2. An earmuff according to claim 1 wherein said C shape half donut sections are comprised of soft material whereby said material possesses properties to allow said C shape half donut sections to conform to various headphone speaker dimensions within the earmuff's headphone speaker space while accomplishing a cooperative releasable attachment around said headphone speaker at their planar sides.

3. An earmuff according to claim 1 wherein said backing surrounds said core element in a close fitted manner and is connected to said C shape half donuts whereby said C shape half donuts may separate at their respective planar sides and hinge upon said backing to open and close together.

4. An earmuff according to claim 3 wherein said donut shaped core element is comprised of said C shaped half donuts connected together at their respective planar sides.

5. An earmuff according to claim 4 wherein said planar sides are defined as the area of the C shape donut halves that touch when said C shape donut halves are connected to form the donut shaped core element.

6. An earmuff according to claim 4 wherein said planar sides (12*a* and 12*b*) sandwich the headphone speaker headband between them while connected together allowing said headphone speaker headband to project out of the earmuff between said planar sides.

7. An earmuff according to claim 4 wherein said planar sides (12*c* and 12*d*) sandwich the headphone speaker wire between them while connected together allowing said speaker wire to project out of the earmuff between said planar sides.

8. An earmuff according to claim 4 wherein said planar sides are releaseably secured by said cooperative connection means.

9. An earmuff according to claim 8 wherein said cooperative connection means is defined by mating hook and loop fasteners on respective facing said planar sides (12A to 12D).

10. An earmuff according to claim 1 wherein said backing extends across the outer surface of said donut shaped core element, said backing and said donut shape core element defines the muff body into which the headphone speaker may be placed.

11. An earmuff according to claim 10 wherein said backing extends across inside planar surfaces and is closely fitted to the shape of each respective C Shape half donut such that the two C shape half donuts may separate.

12. An earmuff according to claim 10 wherein said backing which extends across the outer surface of said donut shaped core element is operative to allow C shape half donuts to swing or hinge apart from each other separating at their planar sides and away from said backing.

13. An Earmuff for use with portable headphone speakers comprised of:

a) a core element comprised of an outer surface, an inside planar surface split into a plurality of sections whereby said sections are releasably connected to each other on their planar sides; and b) said planar sides form a substantially recessed space to accommodate a headphone speaker said sections being releasably connected around said headphone speaker outer circumference; and c) said sections separate and reconnect on hinging means comprising a backing of material coextensive to said outer surface and connected to same.

* * * * *